US008445539B2

(12) United States Patent
Izzo et al.

(10) Patent No.: US 8,445,539 B2
(45) Date of Patent: May 21, 2013

(54) ALPHA-AMINOAMIDE DERIVATIVES USEFUL IN THE TREATMENT OF PSYCHIATRIC DISORDERS

(75) Inventors: Emanuela Izzo, Milan (IT); Laura Faravelli, Garbagnate Milanese (IT); Elena Barbanti, Cologno Monzese (IT); Patricia Salvati, Arese (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 219 days.

(21) Appl. No.: 12/816,143

(22) Filed: Jun. 15, 2010

(65) Prior Publication Data

US 2011/0014304 A1    Jan. 20, 2011

Related U.S. Application Data

(63) Continuation-in-part of application No. PCT/EP2008/066884, filed on Dec. 5, 2008.

(30) Foreign Application Priority Data

Dec. 19, 2007    (EP) ..................................... 07024584

(51) Int. Cl.
*A61K 31/165*    (2006.01)
(52) U.S. Cl.
USPC ....................................................... 514/620
(58) Field of Classification Search
USPC ....................................................... 514/620
See application file for complete search history.

(56) References Cited

U.S. PATENT DOCUMENTS

2007/0203182 A1*    8/2007    Besana et al. .................. 514/317

FOREIGN PATENT DOCUMENTS

| EP | 1870097 | 12/2007 |
| WO | WO 90/14334 | 11/1990 |
| WO | WO 99/26614 | 6/1999 |
| WO | WO 2007/071311 | 6/2007 |
| WO | WO 2007/144153 | 12/2007 |

OTHER PUBLICATIONS

Besana et al. CAS: 143:416265, 2005.*
Bruinvels's CAS: 144: 231108, 2006.*
Baumeister et al. 2002. Historical development of the dopamine hypothesis of schizophrenia. *Journal of the History of the Neurosciences* 11, No. 3 (September): 265-277.
Baylé, et al. 2001. Clinical features of panic attacks in schizophrenia. *European Psychiatry: The Journal of the Association of European Psychiatrists* 16, No. 6 (September): 349-353.
Bunzow et al. 1988. Cloning and expression of a rat D2 dopamine receptor cDNA. *Nature* (Lond) 336:783-787.
Cattabeni, Flaminio. 2004. Ralfinamide. Newron Pharmaceuticals. *IDrugs: The Investigational Drugs Journal* 7, No. 10 (October): 935-939.

Dearry et al. 1990. Molecular cloning and expression of the gene for a human D1 dopamine receptor. *Nature* 347:72-76.
Geyer, et al. 2001. Pharmacological studies of prepulse inhibition models of sensorimotor gating deficits in schizophrenia: a decade in review. *Psychopharmacology* 56, No. 2 (July): 117-154.
Geyer, Mark A. 2006. Are cross-species measures of sensorimotor gating useful for the discovery of procognitive cotreatments for schizophrenia? *Dialogues in Clinical Neuroscience* 8, No. 1: 9-16.
Golombok, et al. 1991. The effects of diazepam on anxiety-related cognition. *Cognitive Therapy and Research* 15, No. 6 (Dec. 1): 459-467.
Hamill, et al. 1981. Improved patch-clamp techniques for high-resolution current recording from cells and cell-free membrane patches. *Pflügers Archiv: European Journal of Physiology* 391, No. 2 (August): 85-100.
Javitt, Daniel C. 2007. Glutamate and schizophrenia: phencyclidine, N-methyl-D-aspartate receptors, and dopamine-glutamate interactions. *International Review of Neurobiology* 78: 69-108.
Large, Charles H. 2007. Do NMDA receptor antagonist models of schizophrenia predict the clinical efficacy of antipsychotic drugs? *Journal of Psychopharmacology* (Oxford, England) 21, No. 3 (May): 283-301.
Lindsley, et al. 2006. Progress towards validating the NMDA receptor hypofunction hypothesis of schizophrenia. *Current Topics in Medicinal Chemistry* 6, No. 8: 771-785.
Morgan, et al. 2004. Acute effects of ketamine on memory systems and psychotic symptoms in healthy volunteers. *Neuropsychopharmacology: Official Publication of the American College of Neuropsychopharmacology* 29, No. 1 (January): 208-218.
Mouri, et al. 2007. Phencyclidine animal models of schizophrenia: approaches from abnormality of glutamatergic neurotransmission and neurodevelopment. *Neurochemistry International* 51, No. 2 (September): 173-184.
Pallanti, et al. 2004. Social anxiety in outpatients with schizophrenia: a relevant cause of disability. *The American Journal of Psychiatry* 161, No. 1 (January): 53-58.
Pevarello et al. 1998. Synthesis and anticonvulsant activity of a new class of 2-[(arylalkyl)amino]alkaneamide derivatives, *J. Med. Chem.* 41:579-590.
Sibley et al. 1992. The molecular biology of dopamine receptors. *Trend Pharmacol. Sci.* 13:61-69.
Sills, T. L. 1999. Amphetamine dose dependently disrupts prepulse inhibition of the acoustic startle response in rats within a narrow time window. *Brain Research Bulletin* 48, No. 4 (Mar. 1): 445-448.
Sokoloff et al. 1990. Molecular cloning and characterization of a novel dopamine receptor (D3) as a target for neuroleptics. *Nature* 347:146-151.

(Continued)

*Primary Examiner* — Rei-tsang Shiao
(74) *Attorney, Agent, or Firm* — Dechert LLP

(57) ABSTRACT

The disclosure relates to pharmacotherapy of a psychiatric disorder which is schizophrenia and/or anxiety, wherein schizophrenia includes schizophrenia related disorders such as brief psychotic disorders, delusional disorders, schizoaffective disorders, and schizophreniform disorders, and anxiety includes panic disorders, obsessive-compulsive disorders (OCD), post-traumatic stress disorders (PTSD), social phobia or social anxiety disorders, specific phobia, and generalized anxiety disorders (GAD). The compounds of the disclosure are useful for the treatment of the above psychiatric disorders alone or in combination with other therapeutical agents effective in the treatment of schizophrenia and/or anxiety disorders.

81 Claims, 2 Drawing Sheets

OTHER PUBLICATIONS

Squires, R. F., and Saederup, E. 1991. A review of evidence for GABergic predominance/glutamatergic deficit as a common etiological factor in both schizophrenia and affective psychoses: more support for a continuum hypothesis of "functional" psychosis. *Neurochemical Research* 16, No. 10 (October): 1099-1111.

Thornberg, S. A., and Saklad, S. R. 1996. A review of NMDA receptors and the phencyclidine model of schizophrenia. *Pharmacotherapy* 16, No. 1 (February): 82-93.

Van Tol et al. 1991. Cloning of the gene for a human dopamine D4 receptor with high affinity for the antipsychotic clozapine. *Nature* 350:610-614.

Van Tol et al. 1992. Multiple dopamine D4 receptor variants in the human population. *Nature* 358:149-152.

Woodruff-Pak, Diana S., and Gould, Thomas J. 2002. Neuronal nicotinic acetylcholine receptors: involvement in Alzheimer's disease and schizophrenia. *Behavioral and Cognitive Neuroscience Reviews* 1, No. 1 (March): 5-20.

* cited by examiner

ALPHA-AMINOAMIDE DERIVATIVES USEFUL IN THE TREATMENT OF PSYCHIATRIC DISORDERS

CROSS REFERENCE TO RELATED APPLICATIONS

This application is a continuation-in-part of application serial no. PCT/EP2008/066884, filed Dec. 5, 2008, which claims the benefit under 35 U.S.C. §§119(a)-(d) and 365(b) of EP07024584.0, filed Dec. 19, 2007, the contents of all of which are incorporated herein by reference in their entireties.

FIELD OF THE INVENTION

The present disclosure relates to alpha-aminoamide derivatives for use in treating psychiatric diseases such as, for example, schizophrenia and/or anxiety.

BACKGROUND

Psychiatric diseases and disorders include, but are not limited to, schizophrenia, schizophreniform disorders, schizoaffective disorders, bipolar disorders (such as bipolar disorders type I, bipolar disorders type II, mania, hypomania), non-bipolar mania, Tourette's syndrome, cyclothymic disorders, rapid cycling, ultradian cycling, personality disorders, attention disorders with or without hyperactive behaviour, delusional disorders, brief psychotic disorders, shared psychotic disorders, psychotic disorders due to a general medical condition, psychotic disorders associated to Parkinson's disease, substance-induced psychotic disorders or a psychotic disorders not otherwise specified, anxiety disorders such as generalised anxiety disorders, panic disorders, post-traumatic stress disorders, impulse control disorders, phobic disorders and dissociative states.

Schizophrenia and related disorders (brief psychotic disorders, delusional disorders, schizoaffective disorders, and schizophreniform disorders) are among the most severe and debilitating forms of psychiatric disorders. As used hereinafter in this description and claims the term "schizophrenia" includes schizophrenia related disorders such as brief psychotic disorders, delusional disorders, schizoaffective disorders, and schizophreniform disorders.

Schizophrenia is characterized by profound disruption of the most fundamental human attributes: language, thought, perception, affect, and sense of self. The array of symptoms frequently includes psychotic manifestations such as hearing internal voices or experiencing other sensations not connected to an obvious source (hallucinations), assigning unusual significance or meaning to normal events (paranoia) or holding fixed false personal beliefs (delusions) and loss of contact with reality. No single symptom is definitive for diagnosis; rather, the diagnosis encompasses a pattern of signs and symptoms, in conjunction with impaired occupational or social functioning.

Generally, symptoms of schizophrenia are categorized as positive, disorganized, negative and cognitive. Positive symptoms are characterized by an excess or distortion of normal functions; negative symptoms, by diminution or loss of normal functions. Disorganized symptoms include thought disorders and bizarre behaviour. Cognitive symptoms are deficits in information processing and problem solving. A person may have symptoms from one or all categories.

However, traditional treatments for schizophrenia are not very effective to treat cognitive deficits in schizophrenia. While it has been reported that more recently developed treatments for schizophrenia, known as "atypical anti-psychotics," may have some effect on cognitive deficits, the effect may not be lasting or not lead to an improvement in daily functioning. In fact there has been little data demonstrating the efficacy of atypical antipsychotics, the most common treatment prescribed for schizophrenia, in the treatment of cognitive impairment, wile psychosocial and cognitive behavioural therapy is still forming the basis of treatment.

On the other hand, disturbance in cognition can be associated with a variety of diseases (e.g., schizophrenia, obsessive compulsive disorders, psychosis, bipolar disorders, anxiety, depression, attention deficit hyperactivity disorder, autism, dyslexia, Tourette's syndrome, Mild Cognitive Impairment (MCI) and disorders of learning in children, adolescents and adults, Age Associated Memory Impairment, Age Associated Cognitive Decline, Alzheimer's Disease, Down's Syndrome, traumatic brain injury, Huntington's Disease, Progressive Supranuclear Palsy (PSP), HIV, stroke, vascular diseases, Pick's or Creutzfeldt-Jacob diseases, multiple sclerosis (MS) and other white matter disorders, Parkinson's Disease) but cannot be identified with the disease itself. However, it is evident for the person skilled in the art that it is essential to distinguish between curing or alleviating a specific symptom, that can be common to a variety of different diseases, and to treat the disease itself.

Different hypotheses have been proposed to try to explain the aetiology of schizophrenia. Various neurotransmitter systems seem to be implicated in the pathology: hyperactivity of the dopaminergic circuits (Baumeister A A, Francis J L, J. Hist. Neurosci.; 2002 September; 11(3): 265-77), imbalance of the gabaergic system (Squires R F, Saederup E, Neurochem. Res., 1991 October; 16(10): 1099-111), NMDA receptor hypo-function state, as well as an impairment of the cholinergic function (Woodruff-Pak D S, Gould T J. Behav. Cogn. Neurosci. Rev. 2002 March; 1(1): 5-20).

Despite major research achievements, the underlying pathophysiology of schizophrenia, including molecular causes and mechanisms, is currently rather incomplete and, in spite of progress in medication of schizophrenia, there are still patients who are resistant to treatments with neuroleptics and mood stabilizers and the unmet medical need is high.

By the late 1970s, it was already clear that the key pharmacological action of antipsychotic drugs was their ability to block dopaminergic D2 receptors, specifically in the mesolimbic dopamine pathway, in that reducing the hyperactivity in this area that is postulated to cause the positive symptoms of psychosis. Unfortunately it is not possible to block dopaminergic overactivity in that specific area only, thus conventional antipsychotics have severe side effects due to the block of D2 receptors in other areas, such as the nigrostriatal pathway, responsible for the control of movements. More recent compounds, such as atypical antipsychotics, have serotonin receptor antagonism on top of D2 receptor antagonism: these characteristics lead to a better disease control with fewer side effects. On the other hand, even if a decrease in dopaminergic tone is considered essential for antipsychotic activity, the modulation of glutamatergic transmission may be equally important. In support to this hypothesis is the fact that symptoms similar to schizophrenia can be induced in healthy volunteers by NMDA antagonists. For decades it has been recognized that the potent NMDA antagonist, phencyclidine (PCP) produces psychotic symptoms in abusers that are remarkably similar to schizophrenia. See Morgan C J et al., Neuropsychopharmacology. 2004 January; 29(1): 208-18; Large C H, J. Psychopharmacol.; 2007 May; 21(3): 283-301.

This data suggests that hypofunction of NMDA receptors might be involved in the generation of negative symptoms of the disease. See also Mouri A et al., Neurochem. Int.; 2007 July-September; 51(2-4): 173-84; Lindsley C W et al., Curr. Top. Med. Chem. 2006; 6(8): 771-85; Thornberg S A, and Saklad S R, Pharmacotherapy.; 1996 January-February; 16(1): 82-93; Javitt D C. Int. Rev. Neurobiol.; 2007 78:69-108.

Patients with schizophrenia, Tourette's syndrome, panic disorders, and obsessive compulsive disorders, exhibit deficits in an operational measure of sensorimotor gating: prepulse inhibition of startle (PPI). See Geyer, Dial. Clin. Neurosci.; 2006 8(1): 9-16; Geyer et al., Psycopharmacology; 2001 July; 156(2-3): 117-54. The reduced ability to filter out among irrelevant auditory stimulation is a characteristic thought to contribute to certain manifestations of these conditions including inattention, distractibility, and cognitive deficits. Similar deficits in PPI are produced in rats by different pharmacological or developmental manipulations. These experimentally induced PPI deficits in rats appear to provide models of sensorimotor gating deficits in schizophrenia patients that have face and predictive validity. In rodents, disruptions in PPI of startle can be produced by: stimulation of dopaminergic (DA) receptors, induced by amphetamine or apomorphine; activation of serotonergic systems, produced by serotonin (5-HT) releasers or direct agonists at multiple serotonin receptors, and blockade of N-methyl-D-aspartate (NMDA) receptors, produced by drugs such as phencyclidine (PCP). Typical and atypical antipsychotics, mood stabilizers, AChE inhibitors and nicotine are effective in restoring PPI disruption induced by the different manipulations.

Anxiety and anxiety related disorders, as specified hereinbelow, cover several different forms of abnormal, pathological anxiety, fears and phobias. Each anxiety related disorder has different symptoms, but all the symptoms cluster around excessive, irrational fear and dread. Anxiety related disorders include panic disorders, obsessive-compulsive disorders (OCD), post-traumatic stress disorders (PTSD), social phobia (or social anxiety disorders), specific phobias, and generalized anxiety disorders (GAD).

The principal medications used for anxiety and anxiety related disorders range from anti-anxiety drugs (benzodiazepines and barbiturates), antidepressants to beta-blockers and have different mechanisms of action. However in some cases there is no correspondence between the therapeutical treatment of the disease and the effect on some of the symptoms which may be associated herewith. For instance, with regard to anxiety related cognition impairments, the results of different studies demonstrate instead that the reduction in anxiety shown by anxious patients after diazepam is not accompanied by a reduction in cognitive disorders. This suggests that diazepam fails to reduce anxiety-related cognitive impairments in clinically anxious subjects. See Cognitive Therapy and Research 1991, 15(6):459-467.

Among the different classes of drugs currently used for the psychiatric disorders above described, many side effects can be observed and therefore a high unmet medical need is perceived for these pathologies. For instance, lithium salts have a narrow therapeutic index; atypical antipsychotics can cause an increased QTc interval and/or weight gain; anticonvulsants cause sedation and cognitive impairments and antidepressants can cause a swing towards mania. Although the side effect profile of each individual drug differs significantly, it is clear that the side-effect profiles of these drugs are far from desirable. Moreover, there are frequently comorbid psychiatric conditions that are also of clinical importance.

Although epidemiological studies report a high prevalence of anxiety and anxiety related disorders in schizophrenia, their clinical relevance is still under recognized. The presence of anxiety in schizophrenia patients has been associated with a greater risk of suicide, poorer social functioning, and an increase risk of relapse. Bayle et al. (Eur Psychiatry 2001; 16-349-353) reported that 47.5% of schizophrenia patients had a lifetime history of panic attacks, that in 31.2% of cases the onset of panic disorder preceded the onset of schizophrenia, and that the treatment of panic disorder improved clinical and social outcome.

While comorbid panic and obsessive-compulsive disorder have been investigated in schizophrenia patients, social anxiety in schizophrenia has received much less clinical attention. People with social anxiety suffer considerable impairments in daily life activities, occupational role, and social relationship. Social anxiety is itself a disabling disorder and individuals with social anxiety disorders as comorbid conditions have a more severe level of disability. Subjects with social anxiety have a higher risk of developing substance/alcohol abuse or dependence and in patients with schizophrenia this is associated to a higher impulsivity and suicidality. Therefore the assessment and treatment of social anxiety disorder comorbidity in schizophrenia patients should improve both clinical and social outcomes. See Pallanti S. et al.—Am J Psychiatry (2004) 161:53-58.

By way of further background, WO90/14334 discloses substituted alpha-aminoamide derivatives active on the central nervous system (CNS) that are useful in the treatment of epilepsy, of Parkinson's disease and as neuroprotective agents in degenerative processes associated with normal ageing or pathological situations, such as brain ischemia; they can also be used as antidepressants, hypnotics and/or antispastic agents. See also Pevarello P. et al. (1998), "Synthesis and anticonvulsant activity of a new class of 2-[(arylalkyl)amino]alkanamide derivatives", J. Med. Chemistry, 41: 579-590.

WO99/26614 discloses substituted alpha-aminoamide derivatives active for the treatment of neuronal damage following global and focal ischemia, for the treatment or prevention of neurodegenerative conditions such as amyotrophic lateral sclerosis (ALS) and for treatment, prevention or amelioration of pain, as anticonvulsant, and as antimanic depressants, as local anesthetics, as antiarrhythmics and for the treatment or prevention of diabetic neuropathy.

WO07/071,311 discloses 2-phenylethylamino derivatives active as calcium and/or sodium channel modulators and therefore useful in preventing alleviating and curing neurological, psychiatric, cardiovascular, inflammatory, ophthalmic, urogenital, and gastrointestinal diseases where the above mechanisms have been described as playing a pathological role.

EP 1870097 A, published on 26 Dec. 2007 and corresponding to WO 2007/144153, published on 21 Dec. 2007, discloses α-aminoamide derivatives for the treatment of cognitive impairment symptoms associated to a variety of neuropsychiatric disorders such as schizophrenia, obsessive compulsive disorders, psychosis, bipolar disorders, anxiety, depression, attention deficit hyperactivity disorder, autism, dyslexia, Tourette's syndrome, Mild Cognitive Impairment (MCI) and disorders of learning in children, adolescents and adults, Age Associated Memory Impairment, Age Associated Cognitive Decline, Alzheimer's Disease, Down's Syndrome, traumatic brain injury, Huntington's Disease, Progressive Supranuclear Palsy (PSP), HIV, stroke, vascular diseases, Pick's or Creutzfeldt-Jacob diseases, multiple sclerosis (MS) and other white matter disorders, Parkinson's Disease.

SUMMARY

The present disclosure relates to therapeutic treatments of psychiatric diseases, such as schizophrenia (including schizophrenia related disorders such as brief psychotic disorders, delusional disorders, schizoaffective disorders, and schizophreniform disorders). The present disclosure also relates to the treatment of anxiety or anxiety related disorders. In aspects of the disclosure, innovative methods for treating psychiatric diseases such as schizophrenia and anxiety with the compounds of this disclosure are provided. The present disclosure also provides methods of treating patients affected by schizophrenia and anxiety or anxiety related disorder using compounds of the disclosure. In some aspects, the compounds of the disclosure may be used in conjunction with a second therapeutic agent to provide an advantageous method of treating one or more diseases including psychiatric diseases.

DETAILED DESCRIPTION

Figure 1:
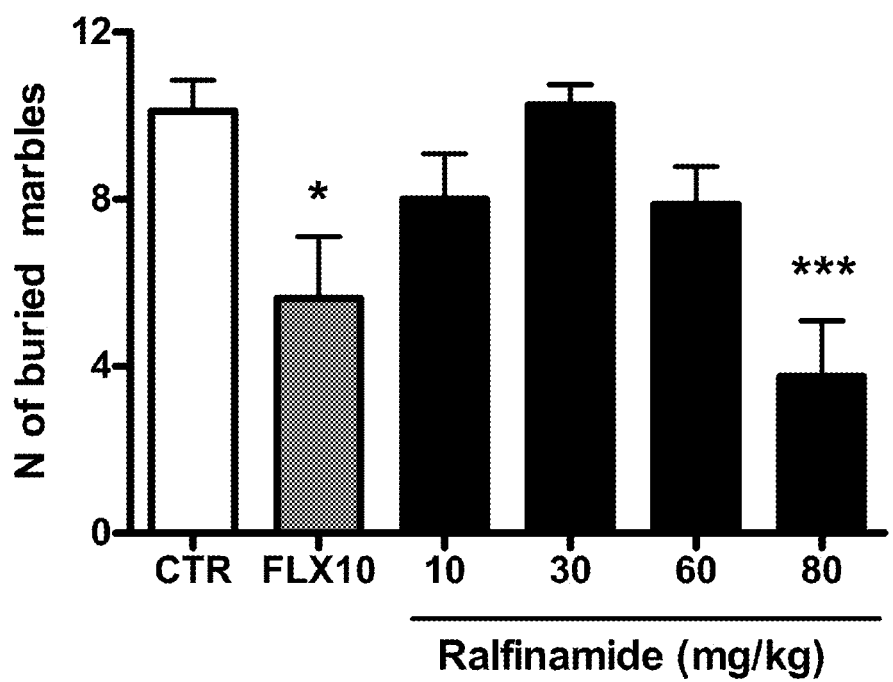
FIG. 1 shows the effect of ralfinamide on the Marble Burying test (statistical evaluation by one-way ANOVA followed by Bonferroni's multiple comparison test; n=6-8 mice per group; *p<0.05; p***<0.001 versus control group)

The present disclosure provides alpha-aminoamide compounds of formula (I)

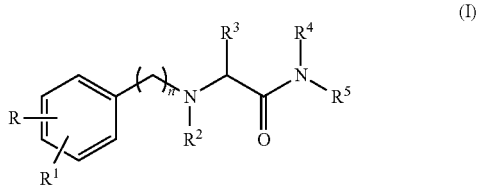

(I)

wherein: n is 1 or 2; R which is in meta or para position, is $C_3$-$C_6$ alkyl or benzyloxy, where the phenyl radical of the benzyloxy group is optionally substituted with fluoro or chloro; $R^1$ is hydrogen, methyl, chloro or fluoro; $R^2$ is hydrogen or $C_1$-$C_3$ alkyl; $R^3$ is hydrogen, $C_1$-$C_4$ alkyl, optionally substituted by hydroxy or methoxy; $R^4$, $R^5$ are, independently, hydrogen or $C_1$-$C_4$ alkyl; if the case, either as a single optically active isomer or a mixture thereof or a pharmaceutically acceptable salt thereof (i.e., single optical isomers thereof; mixtures of single optical isomers thereof; pharmaceutically acceptable salts of single optical isomers thereof; and pharmaceutically acceptable salts of mixtures of single optical isomers thereof) for the use in the treatment of a psychiatric disorder, which is schizophrenia and/or anxiety wherein schizophrenia includes schizophrenia related disorders such as brief psychotic disorders, delusional disorders, schizoaffective disorders, and schizophreniform disorders, and anxiety includes panic disorders, obsessive-compulsive disorders, post-traumatic stress disorders, social phobia or social anxiety disorders, specific phobias, and generalized anxiety disorders.

Accordingly, an object of the disclosure includes the treatment of schizophrenia or anxiety as psychiatric disorder being present alone in a patient as well as the treatment of both schizophrenia and anxiety as psychiatric disorders being concomitantly present in the same patient, i.e. where anxiety is comorbid with schizophrenia.

According to this description and claims the alkyl groups can be branched or straight chain groups.

Pharmaceutically acceptable salts of the compounds of the disclosure include, for example, acid addition salts with inorganic acids, e.g., nitric, hydrochloric, hydrobromic, sulfuric and phosphoric acids and the like, or organic acids, e.g., acetic, propionic, glycolic, lactic, oxalic, malonic, malic, tartaric, citric, succinic, benzoic, cinnamic, mandelic, methanesulfonic, p-toluenesulfonic, salicylic acids, and the like.

Some of the compounds of formula (I) can have asymmetric carbon atoms, and therefore can exist either as individual optically active isomers (enantiomers or diastereoisomers) or mixtures thereof, including racemic mixtures. Accordingly, this application and claims include within their scope all possible optically active isomers, their mixtures, including racemic mixtures.

A further object of the disclosure includes a method for treating a patient affected by a psychiatric disorder which is schizophrenia and/or anxiety wherein schizophrenia includes schizophrenia related disorders such as brief psychotic disorders, delusional disorders, schizoaffective disorders, and schizophreniform disorders, and anxiety includes panic disorders, obsessive-compulsive disorders, post-traumatic stress disorders, social phobia or social anxiety disorders, specific phobias, and generalized anxiety disorders, which comprises administering to said patient in need thereof a therapeutically effective dose of an α-aminoamide of formula (I) as above defined.

Some preferred compounds of formula (I) are those wherein: n is 1 or 2; R which is in meta or para position, is C3-C6 alkyl or benzyloxy, where the phenyl radical of the benzyloxy group is optionally substituted with fluoro or chloro; $R^1$ is hydrogen, methyl, chloro or fluoro; $R^2$ is hydrogen or methyl; $R^3$ is hydrogen, methyl, ethyl, i-propyl, i-butyl, hydroxymethyl, methoxymethyl, 1-hydroxyethyl or 2-hydroxyethyl, 1-methoxyethyl or 2-methoxyethyl; $R^4$, $R^5$ are, independently, hydrogen or $C_1$-$C_3$ alkyl; if the case, either as a single optically active isomer or a mixture thereof or a pharmaceutically acceptable salt thereof.

Examples of preferred compounds of formula (I), which can be used in an effective amount for treating a psychiatric disorder, which is schizophrenia and/or anxiety include, but are not limited to: 2-[3-(2-Fluorobenzyloxy)benzylamino]acetamide; 2-[4-(2-Fluorobenzyloxy)benzylamino]acetamide; 2-[3-(3-Fluorobenzyloxy)benzylamino]acetamide; 2-[4-(3-Fluorobenzyloxy)benzylamino]acetamide; 2-[3-(2-Chlorobenzyloxy)benzylamino]acetamide; 2-[4-(2-Chlorobenzyloxy)benzylamino]acetamide; 2-[3-(3-Chlorobenzyloxy)benzylamino]acetamide; 2-[4-(3-Chlorobenzyloxy)benzylamino]acetamide; 2-[3-(2-Fluorobenzyloxy)benzylamino]propanamide; 2-[4-(2-Fluorobenzyloxy)benzylamino]propanamide; 2-[3-(2-Chlorobenzyloxy)benzylamino]propanamide; 2-[4-(2-Chlorobenzyloxy)benzylamino]propanamide; 2-[3-(3-Fluorobenzyloxy)benzylamino]propanamide; 2-[4-(3-Fluorobenzyloxy)benzylamino]propanamide; 2-[3-(3-Chlorobenzyloxy)benzylamino]propanamide; 2-[4-(3-Chlorobenzyloxy)benzylamino]propanamide; (S)-(+)-2-[3-(2-Fluorobenzyloxy)benzylamino]propanamide; (S)-(+)-2-[4-(2-Fluorobenzyloxy)benzylamino]propanamide; (R)-(−)-2-[3-(2-Fluorobenzyloxy)benzylamino]propanamide; (R)-(−)-

2-[4-(2-Fluorobenzyloxy)benzylamino]propanamide; (S)-(+)-2-[3-(3-Fluorobenzyloxy)benzylamino]propanamide; (S)-(+)-2-[4-(3-Fluorobenzyloxy)benzylamino]propanamide; (R)-(−)-2-[3-(3-Fluorobenzyloxy)benzylamino]propanamide; (R)-(−)-2-[4-(3-Fluorobenzyloxy)benzylamino]propanamide; 2-[3-(2-Fluorobenzyloxy)-4-fluoro-benzylamino]propanamide; 2-[4-(2-Fluorobenzyloxy)-3-fluoro-benzylamino]propanamide; 2-[3-(2-Fluorobenzyloxy)-4-methyl-benzylamino]propanamide; 2-[4-(2-Fluorobenzyloxy)-3-methyl-benzylamino]propanamide; 2-[3-(3-Fluorobenzyloxy)-4-fluoro-benzylamino]propanamide; 2-[4-(3-Fluorobenzyloxy)-3-fluoro-benzylamino]propanamide; 2-[3-(3-Fluorobenzyloxy)-4-methyl-benzylamino]propanamide; 2-[4-(3-Fluorobenzyloxy)-3-methyl-benzylamino]propanamide; 2-[3-(2-Fluorobenzyloxy)benzylamino]-N,N-dimethylpropanamide; 2-[4-(2-Fluorobenzyloxy)benzylamino]-N,N-dimethylpropanamide; 2-[3-(3-Fluorobenzyloxy)benzylamino]-N,N-dimethylpropanamide; 2-[4-(3-Fluorobenzyloxy)benzylamino]-N,N-dimethylpropanamide; 2-[[3-(2-Fluorobenzyloxy)benzylamino]methylamino]propanamide; 2-[[4-(2-Fluorobenzyloxy)benzylamino]methylamino]propanamide; 2-[[3-(3-Fluorobenzyloxy) benzylamino]methylamino]propanamide; 2-[[4-(3-Fluorobenzyloxy)benzylamino]methylamino]propanamide; 2-[3-(2-Fluorobenzyloxy)benzylamino]isovaleramide; 2-[4-(2-Fluorobenzyloxy)benzylamino]isovaleramide; 2-[3-(3-Fluorobenzyloxy)benzylamino]isovaleramide; 2-[4-(3-Fluorobenzyloxy)benzylamino]isovaleramide; 2-[3-(2-Fluorobenzyloxy)benzylamino]-3-hydroxy-propanamide; 2-[4-(2-Fluorobenzyloxy)benzylamino]-3-hydroxy-propanamide; 2-[3-(3-Fluorobenzyloxy)benzylamino]-3-hydroxy-propanamide; 2-[4-(3-Fluorobenzyloxy)benzylamino]-3-hydroxy-propanamide; 2-[3-(2-Fluorobenzyloxy)benzylamino]-3-hydroxy-butanamide; 2-[4-(2-Fluorobenzyloxy)benzylamino]-3-hydroxy-butanamide; 2-[3-(3-Fluorobenzyloxy)benzylamino]-3-hydroxy-butanamide; 2-[4-(3-Fluorobenzyloxy)benzylamino]-3-hydroxy-butanamide; 2-[2-(4-Pentylphenyl)ethylamino]propanamide; 2-[2-[3-(2-Fluorobenzyloxy)phenyl]ethylamino]acetamide; 2-[2-[4-(2-Fluorobenzyloxy)phenyl]ethylamino]acetamide; 2-[2-[3-(3-Fluorobenzyloxy)phenyl]ethylamino]acetamide; 2-[2-[4-(3-Fluorobenzyloxy)phenyl]ethylamino]acetamide; 2-[2-[3-(2-Fluorobenzyloxy)phenyl]ethylamino]propanamide; 2-[2-[4-(2-Fluorobenzyloxy)phenyl]ethylamino]propanamide; 2-[2-[3-(3-Fluorobenzyloxy)phenyl]ethylamino]propanamide; 2-[2-[4-(3-Fluorobenzyloxy)phenyl]ethylamino]propanamide; if the case, either as a single optically active isomer or a mixture thereof or a pharmaceutically acceptable salt thereof.

More preferred compounds of formula (I) include those wherein: n is 1; R which is in meta or para position, is $C_3$-$C_6$ alkyl or benzyloxy, where the phenyl radical of the benzyloxy group is optionally substituted with fluoro; $R^1$ is hydrogen or methyl; $R^2$ is hydrogen; $R^3$ is hydrogen, methyl, i-butyl or hydroxymethyl; $R^4$, $R^5$ are, independently, hydrogen or methyl; if the case, either as a single optically active isomer or a mixture thereof or a pharmaceutically acceptable salt thereof.

Examples of more preferred compounds of formula (I) include, but are not limited to: 2-[3-(2-Fluorobenzyloxy)benzylamino]acetamide; 2-[4-(2-Fluorobenzyloxy)benzylamino]acetamide; 2-[3-(3-Fluorobenzyloxy)benzylamino]acetamide; 2-[4-(3-Fluorobenzyloxy)benzylamino]acetamide; 2-[3-(2-Fluorobenzyloxy)benzylamino]propanamide; 2-[4-(2-Fluorobenzyloxy)benzylamino]propanamide; 2-[3-(3-Fluorobenzyloxy)benzylamino]propanamide; 2-[4-(3-Fluorobenzyloxy)benzylamino]propanamide; (S)-(+)-2-[3-(2-Fluorobenzyloxy)benzylamino]propanamide; (S)-(+)-2-[4-(2-Fluorobenzyloxy)benzylamino]propanamide; (R)-(−)-2-[3-(2-Fluorobenzyloxy)benzylamino]propanamide; (R)-(−)-2-[4-(2-Fluorobenzyloxy)benzylamino]propanamide; (S)-(+)-2-[3-(3-Fluorobenzyloxy)benzylamino]propanamide; (S)-(+)-2-[4-(3-Fluorobenzyloxy)benzylamino]propanamide; (R)-(−)-2-[3-(3-Fluorobenzyloxy)benzylamino]propanamide; (R)-(−)-2-[4-(3-Fluorobenzyloxy)benzylamino]propanamide; 2-[3-(2-Fluorobenzyloxy)-4-methyl-benzylamino]propanamide; 2-[4-(2-Fluorobenzyloxy)-3-methyl-benzylamino]propanamide; 2-[3-(3-Fluorobenzyloxy)-4-methyl-benzylamino]propanamide; 2-[4-(3-Fluorobenzyloxy)-3-methyl-benzylamino]propanamide; 2-[3-(2-Fluorobenzyloxy)benzylamino]-N,N-dimethylpropanamide; 2-[4-(2-Fluorobenzyloxy)benzylamino]-N,N-dimethylpropanamide; 2-[3-(3-Fluorobenzyloxy)benzylamino]-N,N-dimethylpropanamide; 2-[4-(3-Fluorobenzyloxy)benzylamino]-N,N-dimethylpropanamide; 2-[3-(2-Fluorobenzyloxy)benzylamino]isovaleramide; 2-[4-(2-Fluorobenzyloxy)benzylamino]isovaleramide; 2-[3-(3-Fluorobenzyloxy)benzylamino]isovaleramide; 2-[4-(3-Fluorobenzyloxy)benzylamino]isovaleramide; 2-[3-(2-Fluorobenzyloxy)benzylamino]-3-hydroxy-propanamide; 2-[4-(2-Fluorobenzyloxy)benzylamino]-3-hydroxy-propanamide; 2-[3-(3-Fluorobenzyloxy)benzylamino]-3-hydroxy-propanamide; 2-[4-(3-Fluorobenzyloxy)benzylamino]-3-hydroxy-propanamide; 2-[2-(4-Pentylphenyl)ethylamino]propanamide; 2-[2-[3-(2-Fluorobenzyloxy)phenyl]ethylamino]acetamide; 2-[2-[4-(2-Fluorobenzyloxy)phenyl]ethylamino]acetamide; 2-[2-[3-(3-Fluorobenzyloxy)phenyl]ethylamino]acetamide; 2-[2-[4-(3-Fluorobenzyloxy)phenyl]ethylamino]acetamide; if the case, either as a single optically active isomer or a mixture thereof or a pharmaceutically acceptable salt thereof.

Most preferred compounds of formula (I) include those wherein: n is 1; R which is in meta or para position, is $C_3$-$C_6$ alkyl or benzyloxy, where the phenyl radical of the benzyloxy group is optionally substituted with fluoro; $R^1$ and $R^2$ are hydrogen; $R^3$ is hydrogen or methyl; $R^4$, $R^5$ are, independently, hydrogen or methyl; if the case, either as a single optically active isomer or a mixture thereof or a pharmaceutically acceptable salt thereof.

Examples of most preferred compounds of formula (I) are 2-[4-(2-Fluorobenzyloxy)benzylamino]acetamide; 2-[4-(3-Fluorobenzyloxy)benzylamino]acetamide; 2-[4-(2-Fluorobenzyloxy)benzylamino]propanamide; 2-[4-(3-Fluorobenzyloxy)benzylamino]propanamide; (S)-(+)-2-[4-(2-Fluorobenzyloxy)benzylamino]propanamide; (S)-(+)-2-[4-(3-Fluorobenzyloxy)benzylamino]propanamide; (R)-(−)-2-[4-(2-Fluorobenzyloxy)benzylamino]propanamide; (R)-(−)-2-[4-(3-Fluorobenzyloxy)benzylamino]propanamide; 2-[4-(2-Fluorobenzyloxy)-3-methyl-benzylamino]propanamide; 2-[4-(3-Fluorobenzyloxy)-3-methyl-benzylamino]propanamide; 2-[4-(2-Fluorobenzyloxy)benzylamino]-N,N-dimethylpropanamide; 2-[4-(3-Fluorobenzyloxy)benzylamino]-N,N-dimethylpropanamide; 2-[2-(4-Pentylphenyl)ethylamino]propanamide; if the case, either as a single optically active isomer or a mixture thereof or a pharmaceutically acceptable salt thereof.

Specific compounds of formula (I), which are particularly effective for use in treating a psychiatric disorder which is schizophrenia and/or anxiety include: (S)-(+)-2-[4-(2-Fluorobenzyloxy)benzylamino]propanamide; (S)-(+)-2-[4-(3-

Fluorobenzyloxy)benzylamino]propanamide; (R)-(−)-2-[4-(2-Fluorobenzyloxy)benzylamino]propanamide; (R)-(−)-2-[4-(3-Fluorobenzyloxy)benzylamino]propanamide; and the pharmaceutically acceptable salts thereof, preferably the salts with methanesulfonic acid.

Biological Activity

The compounds of the present disclosure have a multiple mechanism of action, including NMDA antagonism, MAO-B inhibition, glutamate release inhibition, DA reuptake inhibition and sodium and/or calcium channel blockade.

A representative compound of this disclosure is "ralfinamide" (S)-(+)-2-[4-(2-fluorobenzyloxy)benzylamino]propanamide, as the salt with methanesulfonic acid, that was found active in schizophrenia (Examples 4 and 5) and in anxiety (Examples 6 and 7) animal models. This effect was surprising, considering the lack of antagonistic effect on dopaminergic (Example 1) receptors and its marked inhibitory activity on MAO-B (Example 2), an enzyme that regulates dopamine metabolism. The inhibition of such enzyme increases the dopamine level in the brain. It is well known in fact that selective MAO-B inhibitors are used in Parkinson's disease for their ability of increasing dopaminergic tone.

Being ralfinamide, a potent MAO-B inhibitor with high brain permeability, one might expect a detrimental effect on schizophrenia. In addition ralfinamide has been shown to be an NMDA antagonist (Example 3) and this would be an additional negative feature for the treatment of schizophrenia, in view of the above mentioned hypothesis of a glutamatergic hypofunction in this pathology. For all these reasons the efficacy of ralfinamide in this schizophrenia model is an unexpected finding.

The ralfinamide dopamine receptor (D1, D2L, D2S, D3, D4.2, D4.4, D4.7 and D5) bindings was measured by radioligand assays (Example 1). The MAO-B activity of ralfinamide was measured by using a radioenzymatic assay in rat brain mitochondria (Example 2). The ralfinamide inhibition of NMDA receptor complex was measured as described in Example 3. The anti-schizophrenia activity was assessed using the "Prepulse inhibition of startle (PPI) in mice" (Example 4) and the "MK-801 induced locomotion in mice" (Example 5) models. The anti anxiety activity was measured using the "Anxiety open field text" in rats (Example 6) and in the "Marble Burying test" (Example 7). The compounds of the disclosure are active in vivo when orally, intraperitoneally or intravenously administered in the range of 0.1 to 200 mg/kg in different animal models here following described.

The compounds of the disclosure may advantageously be used in conjunction with one or more other therapeutic agents effective in the treatment of schizophrenia and/or anxiety. Examples of suitable agents for adjunctive therapy include a serotonin receptor modulator; an AMPA modulator; a nicotinic receptor agonist; a tricyclic antidepressant (e.g., amitryptiline); a monoaminergic uptake inhibitor (e.g., venlafaxine); a cholinesterase inhibitor; an antipsychotic agent, including typical and atypical antipsychotics (e.g., haloperidol, risperidone, clozapine); an anti-depressant, such as a selective serotonin re-uptake inhibitor, serotonin and noradrenaline re-uptake inhibitors; tricyclics antidepressant drugs; a mood stabilizer (e.g., lithium, lamotrigine, valproate); an anxiolytic agent (e.g., benzodiazepines, buspirone, beta-adrenergic receptor antagonists); other calcium or sodium channel blockers.

Of particular interest is the adjunctive treatment comprising administering to a patient affected by schizophrenia, anxiety, or anxiety comorbid with schizophrenia a compound of formula (I), for example, a compound a selected from (S)-(+)-2-[4-(2-fluorobenzyloxy)benzylamino]propanamide; (S)-(+)-2-[4-(3-fluorobenzyloxy)benzylamino]propanamide; (R)-(−)-2-[4-(2-fluorobenzyloxy)benzylamino]propanamide; (R)-(−)-2-[4-(3-fluorobenzyloxy)benzylamino]propanamide; or a pharmaceutically acceptable salt thereof, for example, a salt with methanesulfonic acid, in conjunction with another therapeutic agent. As an example, suitable therapeutic agents for the adjunctive treatment of schizophrenia or anxiety comorbid with schizophrenia include typical and atypical antipsychotics, mood stabilizers, AMPA modulators, serotonin receptor modulators, nicotinic receptor agonists, and cholinesterase inhibitors.

A preferred adjunctive treatment of schizophrenia or anxiety comorbid with schizophrenia in a patient in need thereof comprises the administration to said patient of a compound of formula (I), for example, (S)-(+)-2-[4-(2-fluorobenzyloxy)benzylamino]propanamide (ralfinamide), a pharmaceutically acceptable salt thereof (such as with methanesulfonic acid), in conjunction with another therapeutic agent. Suitable therapeutic agents for the adjunctive treatment of schizophrenia or anxiety comorbid with schizophrenia include typical or atypical antipsychotics, such as haloperidol and risperidone. In one preferred embodiment, haloperidol is used.

In another aspect of the disclosure, a patient affected by schizophrenia or anxiety comorbid with schizophrenia is administered ralfinamide(S)-(+)-2-[4-(2-fluorobenzyloxy)benzylamino]propanamide (ralfinamide), a pharmaceutically acceptable salt thereof (such as with methanesulfonic acid), in conjunction with another therapeutic agent such as a mood stabilizer. Suitable mood stabilizers include lithium, lamotrigine and valproate.

In yet another aspect of the disclosure, a patient affected by anxiety or anxiety comorbid with schizophrenia is administered a compound selected from (S)-(+)-2-[4-(2-fluorobenzyloxy)benzylamino]propanamide; (S)-(+)-2-[4-(3-fluorobenzyloxy)benzylamino]propanamide; (R)-(−)-2-[4-(2-fluorobenzyloxy)benzylamino]propanamide; (R)-(−)-2-[4-(3-fluorobenzyloxy)benzylamino]propanamide; or a pharmaceutically acceptable salt thereof, for example, a salt with methanesulfonic acid, in conjunction with an anxiolytic agent. Suitable anxiolytic agents include benzodiazepines, buspirone, and beta-adrenergic receptor agonists.

Pharmaceutical Compositions

The compounds of the present disclosure are useful in human and veterinary medicaments. It is to be understood that as used herein the terms "treatment" or "treating" whenever not specifically defined otherwise, include prevention, alleviation and cure of pathological affection, in particular, they include both treatment of established symptoms and prophylactic treatment. The compounds of the present disclosure for their therapeutic or preventive use in the above mentioned pathologies will be preferably used as active ingredients in a pharmaceutical composition. Therefore, further objects of the present disclosure are pharmaceutical compositions containing a therapeutically effective amount of a compound of the disclosure or a salt thereof in a mixture with a pharmaceutically acceptable carrier.

Accordingly, the expression "therapeutically effective" when referred to an "amount", a "dose" or "dosage" of the compounds of this disclosure is intended as an "amount", a "dose" or "dosage" of any said compounds sufficient for use in both treatment of the established symptoms and the prophylactic treatment of the above said pathological affections.

The pharmaceutical compositions object of the present disclosure may be administered in a variety of immediate and modified release dosage forms, e.g., orally, in the form of tablets, troches, capsules, sugar or film coated tablets, liquid solutions, emulsions or suspensions; rectally, in the form of suppositories; parenterally, e.g., by intramuscular and/or depot formulations; intravenous injection or infusion; intranasally; locally and transdermally in form of patch and gel and cream.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils, cyclodextrins, polyalkyleneglycols and the like.

The composition comprising the alpha-aminoamide derivatives of formula (I) as above defined can be sterilized and may contain further well known components, such as, for example, preservatives, stabilizers, wetting or emulsifying agents, e.g., paraffin oil, mannide monooleate, salts to adjust osmotic pressure, buffers and the like.

For example, the solid oral forms may contain, together with the active ingredient, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The preparation of the pharmaceutical compositions object of the disclosure can be carried out according to common techniques.

The oral formulations comprise sustained release formulations that can be prepared in conventional manner, for instance by applying an enteric coating to tablets and granules. The liquid dispersion for oral administration may be e.g., syrups, emulsions and suspensions. The syrups may contain as carrier, for example, saccharose or saccharose with glycerine and/or mannitol and/or sorbitol. Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions. The suppositories may contain, together with the active ingredient, a pharmaceutically acceptable carrier, e.g., cocoa butter, polyethylene glycol, a polyoxyethylene sorbitan fatty acid ester surfactants or lecithin.

The pharmaceutical compositions comprising the alpha-aminoamide derivatives of formula (I) as above defined will contain, per dosage unit, e.g., capsule, tablet, powder injection, teaspoonful, suppository and the like from about 0.1 to about 500 mg of one or more active ingredients most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

It is to be understood that while the invention is described in conjunction of the preferred embodiments thereof, those skilled in the art are aware that other embodiments could be made without departing from the spirit of the invention.

EXAMPLES

1. Example 1

Dopamine Receptors Binding Assays-Radioligand Binding Assays

The assays were performed, under standard conditions, as described in the following publications: Dearry A et al., Nature; 1990; 347: 72-76; Bunzow J R et al., Nature; 1988; 336: 783-787; Sokoloff P. et al., Nature; 1990; 347: 146-151; Van Tol H H M et al., Nature; 1991; 350: 610-614; Van Tol H H M et al., Nature; 1992; 358: 149-152; Sibley D R et al., Trend Pharmacol. Sci.; 1992; 13:61-69.

Biochemical assay results are presented as the percent inhibition of specific bindings at a single compound concentration. Responses are considered significant for binding activities >50%.

Ralfinamide, as the methanesulfonate salt, does not show significant binding on the dopamine receptors as shown in Table 1.

TABLE 1

DOPAMINE RECEPTOR BINDING PROFILE
OF RALFINAMIDE METHANESULFONATE

| Receptor type | % Inhibition at 10 μm |
|---|---|
| Dopamine D1 | no inhibition |
| Dopamine D2L | no inhibition |
| Dopamine D2S | no inhibition |
| Dopamine D3 | 7 |
| Dopamine D4.2 | 1 |
| Dopamine D4.4 | no inhibition |
| Dopamine D4.7 | no inhibition |
| Dopamine D5 | no inhibition |

2. Example 2

In Vitro MAO-B Enzyme Activity Assay 2.1. Membrane Preparations (Crude Mitochondrial Fraction)

Male Wistar rats (Harlan, Italy—175-200 g) were sacrificed under light anaesthesia and brains were rapidly removed and homogenized in 8 volumes of ice-cold 0.32 M sucrose buffer containing 0.1 M EDTA, pH 7.4. The crude homogenate was centrifuged at 2220 rpm for 10 minutes at +4° C. and the supernatant recovered. The pellet was homogenized and centrifuged again. The two supernatants were pooled and centrifuged at 9250 rpm for 10 minutes. The pellet was resuspended in fresh buffer and centrifuged at 11250 rpm for 10 minutes at +4° C. The resulting pellet was stored at −80° C.

2.2. In Vitro MAO-B Enzyme Activity Assay—In Vitro Enzyme Activity Assay

The enzyme activity was assessed with a radioenzymatic assay using the substrates $^{14}C$-phenylethylamine (PEA) for MAO-B.

The mitochondrial pellet (500 μg protein) was resuspended in 0.1 M phosphate buffer (pH 7.4). 500 μl of the suspension were added to a 50 μl solution of the test compound or buffer, and incubated for 30 min at 37° C. (preincubation) then the substrate (50 μl) was added. The incubation was carried out for 10 minutes at 37° C. ($^{14}$C-PEA, 0.5 μM).

The reaction was stopped by adding 0.2 mL of 37% HCl or perchloric acid. After centrifugation, the deaminated metabolites were extracted with 3 mL toluene (PEA) and the radioactive organic phase was measured by liquid scintillation spectrometry at 90% efficiency. The amount of neutral and/or acidic metabolites formed as a result of MAO activity was obtained by measuring the radioactivity of the eluate.

The activity of MAO in the sample, corresponding to a percentage of radioactivity compared with the control activity in the absence of the inhibitor, was expressed as nmoles of substrate transformed/mg protein/min. The drug inhibition curves were obtained from at least eight different concentration points, each in duplicate ($10^{-10}$ to $10^{-5}$M). The $IC_{50}$ values (the drug concentration inhibiting 50% of the enzyme activity) were calculated with confidence intervals determined using non linear regression analysis (best fitting aided-computer program). In in vitro enzymatic studies using rat brain mitochondria, ralfinamide, as the methanesulfonate salt, potently inhibited MAO-B with an $IC_{50}$ of 132 nM 3. Example 3

Inhibition of NMDA Receptor Complex 3.1. Materials and Methods for Patch Clamp Experiments On NMDA Receptors 3.1.1. Cell Preparation and Culturing Procedures involving animals and their care were conducted in conformity with institutional guidelines in compliance with national (D.L. n.116, G.U., suppl.40, Feb. 18, 1992) and international laws and policies (EEC Council directive 86/609, OJL358.1, Dec. 12 1987; Guide for the Care and Use of Laboratory Animals, U.S. National Research Council, 1996).

Cortical neurons were prepared from embryonic Wistar rats (E17-E19). A female rat at date 17-19 of pregnancy was anesthetized and sacrificed. The foetuses (n=4-5) were dissected and placed in ice-cold Hank's solution (Hank's solution (Life tech. 14170-088)+glucose 30%+Pen-Strep 100× (Life Tech. 15140-122) 100 U-100 μg/mL and Hepes-NaOH 5 mM).

The brain of the foetuses was cut in two halves, and each cortex was cut in smaller parts with a scissors, the pieces were transferred to a 15 mL centrifuge tube using a 5 mL pipette and washed twice with Hank's solution. The solution was removed except 1-2 mL and the tissue was first dissociated with a 5 mL pipette then with two fire-polished Pasteur pipettes (medium and small opening, respectively).

After the mechanical dissociation, 5 mL of complete DMEM (Dulbecco's modified Eagle medium) (Gibco 41966-029)+FBS (Hyclone) 10%+Glutamine (Life Tech. 25030-024) 2 mM+Pen-Strep 100 U-100 μg/mL were added, and cell suspension was centrifuged for 5 min at 1000 rpm. Supernatant was removed and 5 mL of complete Neurobasal medium was added (NB medium (Life tech. 21103-049)+B27 (Life tech. 17504-044) 2%+Glutamine 2 mM+Pen-Strep 100 U-100 μg/ml).

Cells were counted and diluted in Neurobasal medium to a concentration of 400000 cells per poly-D-lysine 5 μg/mL treated Petri dish. Cortical neurons were used for patch clamp experiments from days 6 to 11 after plating.

3.1.2. Whole Cell Patch Clamp Recordings

Experiments on cortical neurons were carried out using standard whole cell patch clamp methods (Hamill et al., 1981. *Pflügers Archly: European Journal of Physiology* 391(2):85-100). Membrane currents were recorded and filtered at 5 kHz with an Axon Axopatch 200B amplifier and data digitized with an Axon Digidata 1322A (Axon Instruments, CA, USA). Protocol playing and data acquisition were controlled online with Axon pClamp8 software. Measuring and reference electrodes were AgCl—Ag electrodes. A Sutter Instrument P-87 Puller (CA, USA) was used for pulling patch clamp pipettes with a resistance of 2-3 MΩ from Harward borosilicate glass tubes. Cells were continuously superfused with extracellular solutions, using a solution changer Biologic RSC-200.

3.1.3. Solutions and Drugs

External control solution (without $MgCl_2$) consisted of (mM): NaCl 155, KCl 2, $CaCl_2$ 0.5, HEPES 10, glucose 10. $MgCl_2$ was omitted in order to avoid its voltage dependent block.

To stimulate NMDA currents, NMDA and glycine were used as agonist and co-agonist, respectively in the external bath solution (N-methyl-d-aspartic acid Sigma M-3262; glycine Bio Rad 161-07118). Different concentrations were used according to the experimental protocol, as described in the RESULTS chapter. TTX 1 μM (TTX Sigma T-8024) and strychnine 5 μM (Strychnine Sigma S-8753) were also present in order to avoid Na channels and glycine receptor activation, respectively.

Internal solution contained (mM): CsCl 65, CsF 65, NaCl 10, $CaCl_2$ 1.3, $MgCl_2$ 2, HEPES 10, EGTA 10, MgATP 1. Stock solution of ralfinamide methanesulfonate (10 mM) was made in Milli-Q $H_2O$ and diluted to the final concentrations in external solutions.

3.2. Data Analyses

Data were analyzed using Clampfit 9 (Axon Instruments, CA) and Origin 7.5 (Microcal Inc., Northampton, Mass., USA) software. Data points and results were expressed as arithmetic mean±S.E.

In all the experiments −70 mV was used as holding potential. If not differently specified, the control NMDA currents were activated by NMDA 100 μM+glycine 10 μM.

Ralfinamide block was calculated as decrease in the NMDA current after a one-minute-pre-incubation of the compound as compared to the NMDA current obtained in control condition without drug at the same time. Drug concentration-inhibition curves were obtained plotting the fractional blocks versus drug concentrations. Dose-response curves were fitted according to the logistic equation: $y=A2+(A1-A2)/[1+(x/IC_{50})^p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

Ralfinamide, as the methanesulfonate salt, inhibited NMDA-induced currents in primary rat cortical neurons with an $IC_{50}$ of 7.3 μM 4. Example 4

Prepulse Inhibition of Startle in Mice with Disruption by NMDA Receptor Antagonism Prepulse inhibition (PPI) is a cross-species phenomenon (i.e., it is present in mammals ranging from mice to humans), yet it is relatively impaired among schizophrenic patients. The PPI procedure is used to assess the subject's ability to "gate" or filter environmental information. In the acoustic (startle model) of sensorimotor gating a weak acoustic stimulus (prepulse) decrease the reflexive flinching response (startle) produced by a second, more intense, stimulus (the pulse). Drugs like dizocilpine (MK-801) or amphetamine disrupt PPI and represent an animal model of schizophrenia; antipsychotic drugs are able to prevent PPI deficit. The test is quite useful to screen potential antipsychotic drugs.

Methods: Male Wistar rats, weighing 200-300 g were used. Apparatus: All startle and PPI testing has been performed in four startle chambers. Each ventilated illuminated and sound proof chamber contained a clear non-restrictive Plexiglas cylinder resting on a platform. A high-frequency loudspeaker inside the chamber produced both a continuous background noise of 70 dB and the various acoustic stimuli. Vibrations of the Plexiglas cylinder caused by the whole-body startle response of the animal were transduced into analogue signals by a piezoelectric unit attached to the platform. These signals were then digitized and stored by a computer. Sixty-five readings were taken at 1-ms intervals starting at stimulus onset, and the average amplitude was used to determine the acoustic startle response. Sound levels is given in dB.

Prepulse inhibition session: After 5 min of habituation (background white noise, 70 dB), two types of acoustic stimuli were used: acoustic stimulus alone (120 dB, 40 ms) or the stimulus proceeded by a prepulse (76, 79, 82 dB, 40 ms) applied 100 ms before the stimulus. During each experimental session 20 trials of each type were presented with inter-stimulus interval of 20 s. The amplitudes were averaged for each individual animal, separately for both types of trials (stimulus alone or stimulus preceded by the prepulse). The degree of prepulse inhibition was shown as a percentage score (% PPI) calculated as ([(PP+P)/P]×100) a difference between the amplitude of the pulse-alone (P) and the amplitude of the prepulse+pulse trials (PP+P), divided by the amplitude of the pulse-alone trials and multiplied by 100. A high value of the calculated % PPI indicated that the prepulse inhibited the response to a pulse stimulus, whereas a low value indicated weaker inhibition by prepulse. Substances and treatments: MK-801 0.2 mg/kg was dissolved in saline and was given i.p. In each experiment, mice were assigned to receive either compounds of the disclosure or vehicle and were tested in the PPI session using a between-subjects design. The order of drug treatment for the first experiment was test-compound, followed by MK-801; for the second experiment rats received test-compound and then amphetamine. Statistical Analysis: Multiple ANOVA was conducted followed by Dunnett's post hoc test.

Orally administered ralfinamide, as the methanesulfonate salt, at the dose of 90 mg/kg was found active in this experimental model reversing the disruptive effect of MK-801 on PPI as shown in Table 2.

TABLE 2

EFFECT OF RALFINAMIDE METHANESULFONATE ON MK-801-INDUCED PPI DISRUPTION

| Pretreatment | Treatment | Acoustic tone alone | Acoustic pre pulse followed by acoustic tone | Percentage of inhibition |
|---|---|---|---|---|
| Vehicle | Vehicle | 39.00 ± 1.21 | 21.50 ± 0.15 | 44.42 ± 1.33 |
| Vehicle | MK-801 0.2 mg/kg | 40.50 ± 1.96 | 37.00 ± 2.11 | 9.07 ± 0.81# |
| Ralfinamide methane-sulfonate 90 mg/kg | Vehicle | 35.50 ± 0.45 | 20.00 ± 1.51 | 44.16 ± 3.54 |

TABLE 2-continued

EFFECT OF RALFINAMIDE METHANESULFONATE ON MK-801-INDUCED PPI DISRUPTION

| Pretreatment | Treatment | Acoustic tone alone | Acoustic pre pulse followed by acoustic tone | Percentage of inhibition |
|---|---|---|---|---|
| Ralfinamide methane-sulfonate 90 mg/kg | MK-801 0.2 mg/kg | 38.50 ± 1.36 | 30.00 ± 0.90 | 21.92 ± 0.40* |

All data are given as arithmetical means ± SEM.
indicates statistically significant difference between Vehicle and Vehicle treated animals and animals injected with MK-801 in the respect to percentage of inhibition.
*indicates statistically significant differences between Vehicle + MK-801 treated animals and animals treated with ralfinamide methanesulfonate. Analysis of variance followed by Dunnet test.

5. Example 5

MK-801 Induced Hyperlocomotion in Mice

Glutamate N-methyl-D-aspartate (NMDA) receptor antagonists, like phencyclidine (PCP) or MK-801, elicit schizophrenia-like symptoms in humans and behavioural abnormalities in animals, such as hyperactivity. Atypical antipsychotics decrease hyperlocomotion produced in mice by MK-801 or PCP and this represents a commonly used animal models predictive of efficacy against the symptoms of schizophrenia. Vehicle or compound was injected 30-35 min before the animal entered the activity chambers. Hyperlocomotion was produced in mice by administration of MK-801 (0.3 mg/kg) 15 min before the animal entered the activity chambers (i.e., 20-45 min after vehicle or compound administration) and the total distance traveled in centimeters was determined during a 15-30 min session. The increase in MK-801-induced total distance traveled were attenuated by active compounds.

6. Example 6

Anxiety Open Field Test

The Open Field test is commonly used to assess locomotor, exploratory and anxiety-like behaviour in rats or mice. This test is particularly useful in evaluating the effects of anxiolytic and anxiogenic drugs, locomotor responses to drug and as well as behavioural responses to novelty.

The Open Field test task approaches the conflict between the innate fear that rats have of the central area of a novel or brightly lit open field versus their desire to explore new environments. When anxious, the natural tendency of rodents is to prefer staying closed to the walls (thigmotaxis). In this context, anxiety-related behaviour is measured by the degree to which the rat avoids the center of the Open Field test.

The Open Field arena consists of an empty and bright square arena surrounded by walls to prevent animal from escaping. The arena (90 cm×90 cm×40 cm height) was divided into 6×6 grid of equally-sized squares using black tape.

The outer section of the box is defined as the sum of all squares adjacent to a wall (i.e. 16 out of 36 squares, not including the 4 corner squares). The central region of the box (16 squares) is subdivided into a large (LC) and a small centre (SC) of 12 and 4 squares respectively.

The rat is placed in the center of the arena and its behaviour recorded on video over a chosen period (from 5 to 15 min) and scored.

Time spent in each category of square is recorded. In addition, the fifteen minute open-field test is divided into 3 blocks of 5 minutes and total locomotor activity is scored as the number of square entries in each five minute block. In addition, the frequency of the following behaviours is recorded: stretched attend posture (stretching forward with the forelimbs extended, often with the back arched in order to maintain a low profile), rearing (standing on hind legs, with or without contact with the sides of the arena), grooming (using paws or tongue to clean/scratch body) and corner facing (i.e. standing or sitting with the face directed toward the corner of the box). Finally, the latency to visit the large centre and any one of the four corners is scored manually.

The rats receiving anti-anxiety compounds explore the center of the Open Field more than control rats that prefer to stay along the walls.

7. Example 7

Marble Burying Test

The Marble Burying Test is considered an animal model of anxiety/obsessive-compulsive disorder (OCD). Mice which are placed individually in a cage containing a number of glass marbles spontaneously tend to bury the glass marbles present.

Several compounds which attenuate anxiety, depression, psychosis or obsessive-compulsive disorders affect this behaviour reducing the number of marbles buried. Therefore the test has predictive validity for anti-anxiety and anti-OCD potential compounds.

CD1 mice were injected with ralfinamide at the doses of 10, 30, 60 and 80 mg/kg, po; fluoxetine (FLX) at 10 mg/kg, sc or saline and returned to their home cage. After 30 min (ralfinamide) or 60 min (fluoxetine), mice were individually placed in a new cage contained 12 evenly spaced glass marbles. After 30 min mice were removed from the cages and the number of glasses buried for at least two-thirds in the sawdust was counted.

FIG. 1 shows the effect of ralfinamide on the Marble Burying test determined under the following conditions and statistical evaluations:

One-way ANOVA followed by Bonferroni's multiple comparison test; n=6-8 mice per group *p<0.05; p***<0.001 versus control group CTR: Controls group
FLX: Group receiving fluoxetine (10 mg/kg, sc.)
FIG. 1 also demonstrates that ralfinamide at the dose of 80 mg/kg po significantly reduces the number of buried marbles.

8. Example 8

Ralfinamide Methanesulfonate and Haloperidol Association in a Model of PPI Deficit The effects of ralfinamide methanesulfonate (Ralf) and its combination with subthreshold doses of the benchmark antipsychotic agent haloperidol (Halo) on the disruption of the prepulse inhibition (PPI) of acoustic startle reflex mediated by d-amphetamine (Amph) was evaluated. The prepulse inhibition of the startle response provides an operational measure of sensorimotor gating in which a weak stimulus presented prior to a startling stimulus reduces the startle response. Prepulse inhibition deficits have been observed in patients with neuropsychiatric disorders, including schizophrenia. In animals, prepulse inhibition can be disrupted by a number of pharmacological treatments that are known to induce psychotomimetic reaction, such as with Amph. Remarkably, this alteration has been shown to be countered by all major antipsychotic compounds, highlighting Amph-mediated PPI deficit as a dependable and powerful animal model of psychotic-like behavior. See, e.g., Sills, T L. 1999. Amphetamine dose dependently disrupts prepulse inhibition of the acoustic startle response in rats within a narrow time window. Brain Research Bulletin 48, no. 4 (March 1): 445-448.

A PPI test, carried out according to the method described in Example 4, was performed in rats. Ralfinamide methanesulfonate per se, at 60 mg/kg p.o. (corresponding to plasma levels of 3.2 μM) and haloperidol administered at a dose of 0.05 mg/kg, i.p. did not reverse the PPI impairment induced by d-amphetamine (2.5 mg/kg, s.c.).

Figure 2:
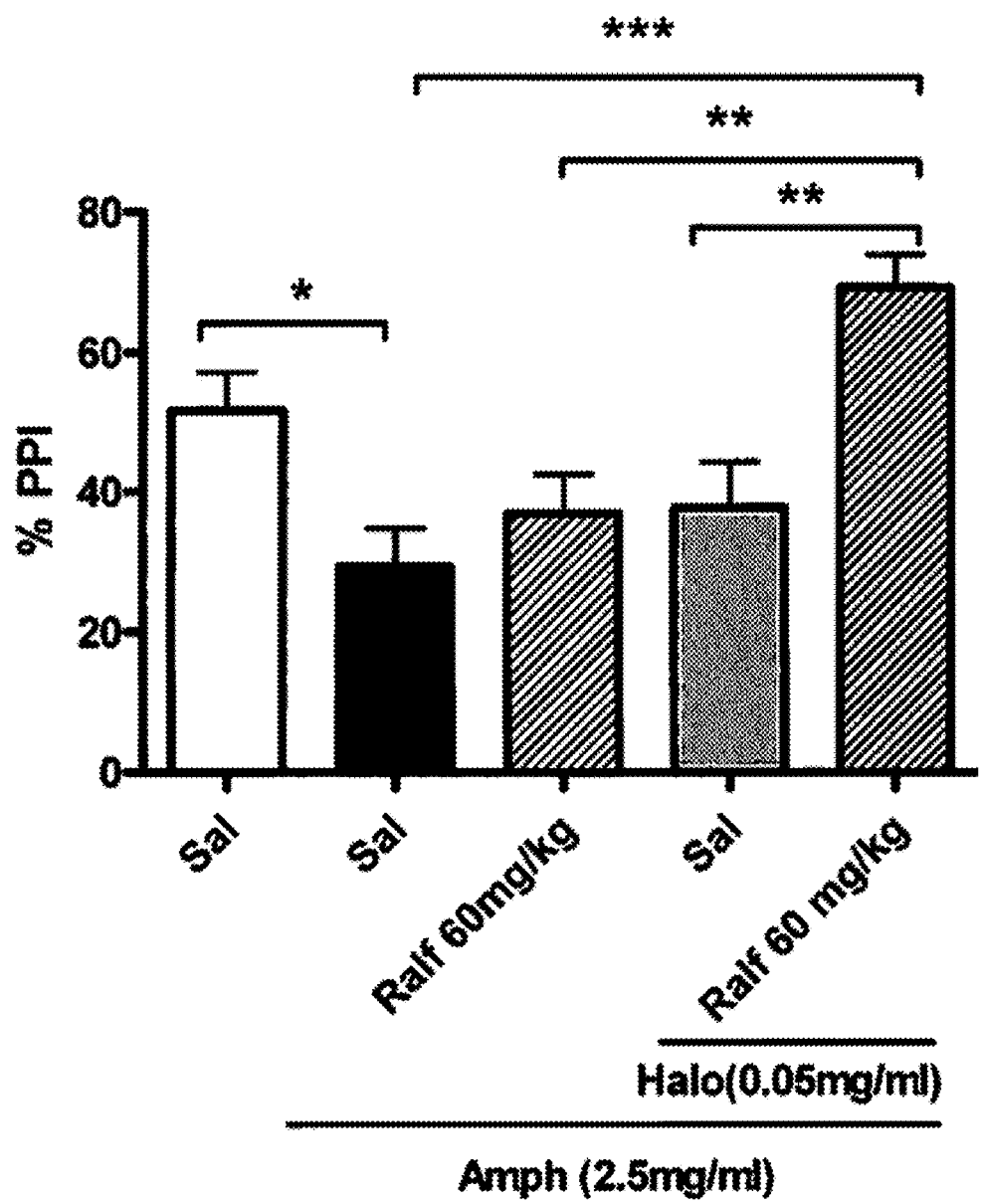
FIG. 2 shows the effect of ralfinamide and haloperidol on amphetamine-induced PPI deficits (values represent mean±SEM for each treatment; for all groups, n=8-12 and Sal=vehicle; statistical evaluation by one-way ANOVA followed by Bonferroni's post hoc analysis comparing selected pairs of columns; *p<0.05, p<0.01; *p<0.001).

Instead, the association of ralfinamide methanesulfonate with the sub-threshold dose of haloperidol produced a complete reversal of PPI deficit. See FIG. 2. The effect was also statistically significant when compared to ralfinamide methanesulfonate or haloperidol alone, suggesting a synergistic effect of the two drugs.

The data suggests that ralfinamide methanesulfonate may potentiate the therapeutic actions of typical antipsychotic agents and could represent a therapeutical option for schizophrenic patients.

We claim:
1. A method of treating schizophrenia or a schizophrenia related disorder, comprising administering to a patient in need thereof a therapeutically effective dose of a compound of formula (I)

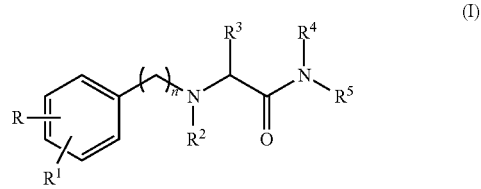

or its single optical isomers or mixtures thereof or pharmaceutically acceptable salts of its single optical isomers or mixtures thereof, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or $C_1$-$C_3$ alkyl;
$R^3$ is hydrogen or $C_1$-$C_4$ alkyl optionally substituted by hydroxy or methoxy;
$R^4$ and $R^5$ are, independently, hydrogen or $C_1$-$C_4$ alkyl.
2. The method of claim 1, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or methyl;
$R^3$ is hydrogen, methyl, ethyl, i-propyl, i-butyl, hydroxymethyl, methoxymethyl, 1-hydroxyethyl, 2-hydroxyethyl, 1-methoxyethyl or 2-methoxyethyl; and
$R^4$ and $R^5$ are, independently, hydrogen or $C_1$-$C_3$ alkyl.

3. The method of claim 1, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ is hydrogen or methyl;
$R^2$ is hydrogen;
$R^3$ is hydrogen, methyl, i-butyl or hydroxymethyl; and
$R^4$ and $R^5$ are, independently, hydrogen or methyl.

4. The method of claim 1, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ and $R^2$ are hydrogen;
$R^3$ is hydrogen or methyl; and
$R^4$, $R^5$ are, independently, hydrogen or methyl.

5. The method of claim 1, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-chlorobenzyloxy)benzylamino]acetamide;
2-[4-(2-chlorobenzyloxy)benzylamino]acetamide;
2-[3-(3-chlorobenzyloxy)benzylamino]acetamide;
2-[4-(3-chlorobenzyloxy)benzylamino]acetamide;
2-[3-(2-fluorobenzyloxy)benzylamino]propanamide;
2-[4-(2-fluorobenzyloxy)benzylamino]propanamide;
2-[3-(2-chlorobenzyloxy)benzylamino]propanamide;
2-[4-(2-chlorobenzyloxy)benzylamino]propanamide;
2-[3-(3-fluorobenzyloxy)benzylamino]propanamide;
2-[4-(3-fluorobenzyloxy)benzylamino]propanamide;
2-[3-(3-chlorobenzyloxy)benzylamino]propanamide;
2-[4-(3-chlorobenzyloxy)benzylamino]propanamide;
(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-fluoro-benzylamino]propanamide;
2-[4-(2-fluorobenzyloxy)-3-fluoro-benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-fluoro-benzylamino]propanamide;
2-[4-(3-fluorobenzyloxy)-3-fluoro-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[[3-(2-fluorobenzyloxy)benzylamino]methylamino]propanamide;
2-[[4-(2-fluorobenzyloxy)benzylamino]methylamino]propanamide;
2-[[3-(3-fluorobenzyloxy)benzylamino]methylamino]propanamide;
2-[[4-(3-fluorobenzyloxy)benzylamino]methylamino]propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[3-(2-fluorobenzyloxy)benzylamino]-3-hydroxy-butanamide;
2-[4-(2-fluorobenzyloxy)benzylamino]-3-hydroxy-butanamide;
2-[3-(3-fluorobenzyloxy)benzylamino]-3-hydroxy-butanamide;
2-[4-(3-fluorobenzyloxy)benzylamino]-3-hydroxy-butanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
2-[2-[3-(2-fluorobenzyloxy)phenyl]ethylamino]propanamide;
2-[2-[4-(2-fluorobenzyloxy)phenyl]ethylamino]propanamide;
2-[2-[3-(3-fluorobenzyloxy)phenyl]ethylamino]propanamide;
2-[2-[4-(3-fluorobenzyloxy)phenyl]ethylamino]propanamide;
single optical isomers thereof; and mixtures of single optical isomers thereof.

6. The method of claim 1, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-fluorobenzyloxy)benzylamino]propanamide;
2-[4-(2-fluorobenzyloxy)benzylamino]propanamide;
2-[3-(3-fluorobenzyloxy)benzylamino]propanamide;
2-[4-(3-fluorobenzyloxy)benzylamino]propanamide;

(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
single optical isomers thereof; and mixtures of single optical isomers thereof.

7. The method of claim 1, wherein the compound or its pharmaceutically acceptable salt is selected from:
2-[4-(2-fluorobenzyloxy)benzylamino]acetamide;
2-[4-(3-fluorobenzyloxy)benzylamino]acetamide;
2-[4-(2-fluorobenzyloxy)benzylamino]propanamide;
2-[4-(3-fluorobenzyloxy)benzylamino]propanamide;
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide;
2-[4-(2-fluorobenzyloxy)-3-methyl-benzylamino]propanamide;
2-[4-(3-fluorobenzyloxy)-3-methyl-benzylamino]propanamide;
2-[4-(2-fluorobenzyloxy)benzylamino]-N,N-dimethyl-propanamide;
2-[4-(3-fluorobenzyloxy)benzylamino]-N,N-dimethyl-propanamide;
2-[2-(4-pentylphenyl)ethylamino]propanamide;
single optical isomers thereof; and mixtures of single optical isomers thereof.

8. The method of claim 1, wherein the compound or its pharmaceutically acceptable salt is selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide; and
(R)-(−)-2-[4-(3-fluorobenzyloxy)benzylamino]propanamide.

9. The method of claim 1, wherein the compound is selected from:
(S)-(+)-2-[4-(2-fluorobenzyloxy)benzylamino]propanamide or the pharmaceutically acceptable salt thereof with methanesulfonic acid.

10. The method of claim 1, wherein the compound is a pharmaceutically acceptable salt with methanesulfonic acid.

11. The method of claim 1, wherein said schizophrenia related disorder is brief psychotic disorder, delusional disorder, schizoaffective disorder or schizophreniform disorder.

12. The method of claim 1, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

13. The method of claim 12, wherein the compound is (S)-(+)-2-[4-(2-fluorobenzyloxy)benzylamino]propanamide or the pharmaceutically acceptable salt thereof, and the second therapeutic agent is haloperidol or risperidone.

14. The method of claim 13, wherein the pharmaceutically acceptable salt is the salt with methanesulfonic acid, and the second therapeutic agent is haloperidol.

15. The method of claim 12, wherein the second therapeutic agent is lithium, lamotrigine or valproate.

16. A method of treating schizophrenia or a schizophrenia related disorder, comprising administering to a patient in need thereof of a therapeutically effective dose of a compound selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide; or a pharmaceutically thereof.

17. The method of claim 16, wherein the compound is a pharmaceutically acceptable salt with methanesulfonic acid.

18. The method of claim 16, wherein said schizophrenia related disorder is brief psychotic disorder, delusional disorder, schizoaffective disorder or schizophreniform disorder.

19. The method of claim 16, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

20. The method of claim 19, where the second therapeutic agent is haloperidol or risperidone.

21. The method of claim 20, where the second therapeutic agent is haloperidol.

22. The method of claim 19, where the second therapeutic agent is lithium, lamotrigine or valproate.

23. A method of treating schizophrenia or a schizophrenia related disorder, comprising administering to a patient in need thereof of a therapeutically effective dose of
(S)-(+)-2-[4-(2-fluorobenzyloxy)benzylamino]propanamide or
the pharmaceutically acceptable salt thereof with methanesulfonic acid.

24. The method of claim 23, wherein said schizophrenia related disorder is brief psychotic disorder, delusional disorder, schizoaffective disorder or schizophreniform disorder.

25. The method of claim 23, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

26. The method of claim 25, wherein the second therapeutic agent is haloperidol or risperidone.

27. The method of claim 26, wherein the second therapeutic agent is haloperidol.

28. The method of claim 25, wherein the second therapeutic agent is lithium, lamotrigine or valproate.

29. A method of treating anxiety or an anxiety related disorder, comprising administering to a patient in need thereof a therapeutically effective dose of a compound of formula (I)

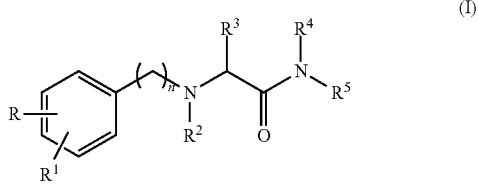

or its single optical isomers or mixtures thereof or pharmaceutically acceptable salts of its single optical isomers or mixtures thereof, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or $C_1$-$C_3$ alkyl;
$R^3$ is hydrogen or $C_1$-$C_4$ alkyl optionally substituted by hydroxy or methoxy;
$R^4$ and $R^5$ are, independently, hydrogen or $C_1$-$C_4$ alkyl.

30. The method of claim 29, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or methyl;
$R^3$ is hydrogen, methyl, ethyl, i-propyl, i-butyl, hydroxymethyl, methoxymethyl, 1-hydroxyethyl, 2-hydroxyethyl, 1-methoxyethyl or 2-methoxyethyl; and
$R^4$ and $R^5$ are, independently, hydrogen or $C_1$-$C_3$ alkyl.

31. The method of claim 29, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ is hydrogen or methyl;
$R^2$ is hydrogen;
$R^3$ is hydrogen, methyl, i-butyl or hydroxymethyl; and
$R^4$ and $R^5$ are, independently, hydrogen or methyl.

32. The method of claim 29, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ and $R^2$ are hydrogen;
$R^3$ is hydrogen or methyl; and
$R^4$, $R^5$ are, independently, hydrogen or methyl.

33. The method of claim 29, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-chlorobenzyloxy)benzylamino]acetamide;
2-[4-(2-chlorobenzyloxy)benzylamino]acetamide;
2-[3-(3-chlorobenzyloxy)benzylamino]acetamide;
2-[4-(3-chlorobenzyloxy)benzylamino]acetamide;
2-[3-(2-fluorobenzyloxy)benzylamino]propanamide;
2-[4-(2-fluorobenzyloxy)benzylamino]propanamide;
2-[3-(2-chlorobenzyloxy)benzylamino]propanamide;
2-[4-(2-chlorobenzyloxy)benzylamino]propanamide;
2-[3-(3-fluorobenzyloxy)benzylamino]propanamide;
2-[4-(3-fluorobenzyloxy)benzylamino]propanamide;
2-[3-(3-chlorobenzyloxy)benzylamino]propanamide;
2-[4-(3-chlorobenzyloxy)benzylamino]propanamide;
(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-fluoro-benzylamino]propanamide;
2-[4-(2-fluorobenzyloxy)-3-fluoro-benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-fluoro-benzylamino]propanamide;

2-[4-(3-fluorobenzyloxy)-3-fluoro-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[[3-(2-fluorobenzyloxy)benzylamino]methylamino]propanamide;
2-[[4-(2-fluorobenzyloxy)benzylamino]methylamino]propanamide;
2-[[3-(3-fluorobenzyloxy)benzylamino]methylamino]propanamide;
2-[[4-(3-fluorobenzyloxy)benzylamino]methylamino]propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[3-(2-fluorobenzyloxy)benzylamino]-3-hydroxy-butanamide;
2-[4-(2-fluorobenzyloxy)benzylamino]-3-hydroxy-butanamide;
2-[3-(3-fluorobenzyloxy)benzylamino]-3-hydroxy-butanamide;
2-[4-(3-fluorobenzyloxy)benzylamino]-3-hydroxy-butanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
2-[2-[3-(2-fluorobenzyloxy)phenyl]ethylamino]propanamide;
2-[2-[4-(2-fluorobenzyloxy)phenyl]ethylamino]propanamide;
2-[2-[3-(3-fluorobenzyloxy)phenyl]ethylamino]propanamide;
2-[2-[4-(3-fluorobenzyloxy)phenyl]ethylamino]propanamide;
single optical isomers thereof; and mixtures of single optical isomers thereof.

34. The method of claim 29, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-fluorobenzyloxy)benzylamino]propanamide;
2-[4-(2-fluorobenzyloxy)benzylamino]propanamide;
2-[3-(3-fluorobenzyloxy)benzylamino]propanamide;
2-[4-(3-fluorobenzyloxy)benzylamino]propanamide;
(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
single optical isomers thereof; and mixtures of single optical isomers thereof.

35. The method of claim 29, wherein the compound or its pharmaceutically acceptable salt is selected from:
2-[4-(2-fluorobenzyloxy)benzylamino]acetamide;
2-[4-(3-fluorobenzyloxy)benzylamino]acetamide;
2-[4-(2-fluorobenzyloxy)benzylamino]propanamide;
2-[4-(3-fluorobenzyloxy)benzylamino]propanamide;
(S)-(+)-2-[4-(2-fluorobenzyloxy)benzylamino]propanamide;

(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide;
2-[4-(2-fluorobenzyloxy)-3-methyl-benzylamino]propanamide;
2-[4-(3-fluorobenzyloxy)-3-methyl-benzylamino]propanamide;
2-[4-(2-fluorobenzyloxy)benzylamino]-N,N-dimethyl-propanamide;
2-[4-(3-fluorobenzyloxy)benzylamino]-N,N-dimethyl-propanamide;
2-[2-(4-pentylphenyl)ethylamino]propanamide;
single optical isomers thereof; and mixtures of single optical isomers thereof.

36. The method of claim 29, wherein the compound or its pharmaceutically acceptable salt is selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide; and
(R)-(−)-2-[4-(3-fluorobenzyloxy)benzylamino]propanamide.

37. The method of claim 29, wherein the compound is selected from:
(S)-(+)-2-[4-(2-fluorobenzyloxy)benzylamino]propanamide
or the pharmaceutically acceptable salt thereof with methanesulfonic acid.

38. The method of claim 29, wherein the compound is a pharmaceutically acceptable salt with methanesulfonic acid.

39. The method of claim 29, wherein said anxiety or anxiety related disorder is panic disorder, obsessive-compulsive disorder, post-traumatic stress disorder, social or other phobia, social anxiety disorder or generalized anxiety disorder.

40. The method of claim 29, further comprising administering of a second therapeutic agent which is an anxiolytic agent.

41. The method of claim 40, wherein the compound is (S)-(+)-2-[4-(2-fluorobenzyloxy)benzylamino]propanamide or the pharmaceutically acceptable salt thereof with methanesulfonic acid and the anxiolytic agent is a benzodiazepine, buspirone, or a beta-adrenergic receptor agonist.

42. A method of treating anxiety or an anxiety related disorder, comprising administering to a patient in need thereof of a therapeutically effective dose of a compound selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide; or a pharmaceutically acceptable salt thereof.

43. The method of claim 42, wherein the compound is a pharmaceutically acceptable salt with methanesulfonic acid.

44. The method of claim 42, wherein said anxiety or anxiety related disorder is panic disorder, obsessive-compulsive disorder, post-traumatic stress disorder, social or other phobia, social anxiety disorder or generalized anxiety disorder.

45. The method of claim 42, further comprising administering of a second therapeutic agent which is an anxiolytic agent.

46. The method of claim 45, wherein the compound is (S)-(+)-2-[4-(2-fluorobenzyloxy)benzylamino]propanamide or the pharmaceutically acceptable salt thereof with methanesulfonic acid and the anxiolytic agent is a benzodiazepine, buspirone, or a beta-adrenergic receptor agonist.

47. A method of treating anxiety or an anxiety related disorder, comprising administering to a patient in need thereof of a therapeutically effective dose of
(S)-(+)-2-[4-(2-fluorobenzyloxy)benzylamino]propanamide or
the pharmaceutically acceptable salt thereof with methanesulfonic acid.

48. The method of claim 47, wherein said anxiety or anxiety related disorder is panic disorder, obsessive-compulsive disorder, post-traumatic stress disorder, social or other phobia, social anxiety disorder or generalized anxiety disorder.

49. The method of claim 47, further comprising administering of a second therapeutic agent which is an anxiolytic agent.

50. The method of claim 49, wherein the anxiolytic agent is a benzodiazepine, buspirone, or a beta-adrenergic receptor agonist.

51. A method of treating schizophrenia combined with anxiety, comprising administering to a patient in need thereof a therapeutically effective dose of a compound of formula (I)

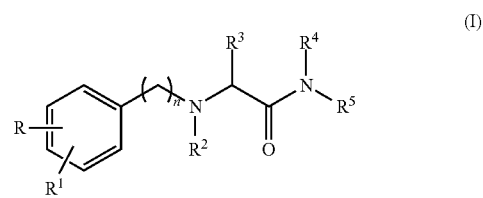

or its single optical isomers or mixtures thereof or pharmaceutically acceptable salts of its single optical isomers or mixtures thereof, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or $C_1$-$C_3$ alkyl;
$R^3$ is hydrogen or $C_1$-$C_4$ alkyl optionally substituted by hydroxy or methoxy;
$R^4$ and $R^5$ are, independently, hydrogen or $C_1$-$C_4$ alkyl.

52. The method of claim 51, wherein:
n is 1 or 2;
R is meta or para to the alpha-aminoamide substituent and is a $C_3$-$C_6$ alkyl or benzyloxy, wherein the phenyl radical of the benzyloxy group is optionally substituted with fluoro or chloro;
$R^1$ is hydrogen, methyl, chloro or fluoro;
$R^2$ is hydrogen or methyl;
$R^3$ is hydrogen, methyl, ethyl, i-propyl, i-butyl, hydroxymethyl, methoxymethyl, 1-hydroxyethyl, 2-hydroxyethyl, 1-methoxyethyl or 2-methoxyethyl; and
$R^4$ and $R^5$ are, independently, hydrogen or $C_1$-$C_3$ alkyl.

53. The method of claim 51, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ is hydrogen or methyl;
$R^2$ is hydrogen;
$R^3$ is hydrogen, methyl, i-butyl or hydroxymethyl; and
$R^4$ and $R^5$ are, independently, hydrogen or methyl.

54. The method of claim 51, wherein:
n is 1;
R is meta or para to the alpha-aminoamide substituent and is a $C_3$-$C_6$ alkyl or benzyloxy, wherein the phenyl radical of the benzyloxy group is optionally substituted with fluoro;
$R^1$ and $R^2$ are hydrogen;
$R^3$ is hydrogen or methyl; and
$R^4$, $R^5$ are, independently, hydrogen or methyl.

55. The method of claim 51, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-chlorobenzyloxy)benzylamino]acetamide;
2-[4-(2-chlorobenzyloxy)benzylamino]acetamide;
2-[3-(3-chlorobenzyloxy)benzylamino]acetamide;
2-[4-(3-chlorobenzyloxy)benzylamino]acetamide;
2-[3-(2-fluorobenzyloxy)benzylamino]propanamide;
2-[4-(2-fluorobenzyloxy)benzylamino]propanamide;
2-[3-(2-chlorobenzyloxy)benzylamino]propanamide;
2-[4-(2-chlorobenzyloxy)benzylamino]propanamide;
2-[3-(3-fluorobenzyloxy)benzylamino]propanamide;
2-[4-(3-fluorobenzyloxy)benzylamino]propanamide;
2-[3-(3-chlorobenzyloxy)benzylamino]propanamide;
2-[4-(3-chlorobenzyloxy)benzylamino]propanamide;
(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-fluoro-benzylamino]propanamide;
2-[4-(2-fluorobenzyloxy)-3-fluoro-benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-fluoro-benzylamino]propanamide;
2-[4-(3-fluorobenzyloxy)-3-fluoro-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[[3-(2-fluorobenzyloxy)benzylamino]methylamino]propanamide;
2-[[4-(2-fluorobenzyloxy)benzylamino]methylamino]propanamide;
2-[[3-(3-fluorobenzyloxy)benzylamino]methylamino]propanamide;
2-[[4-(3-fluorobenzyloxy)benzylamino]methylamino]propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[3-(2-fluorobenzyloxy)benzylamino]-3-hydroxy-butanamide;
2-[4-(2-fluorobenzyloxy)benzylamino]-3-hydroxy-butanamide;
2-[3-(3-fluorobenzyloxy)benzylamino]-3-hydroxy-butanamide;
2-[4-(3-fluorobenzyloxy)benzylamino]-3-hydroxy-butanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
2-[2-[3-(2-fluorobenzyloxy)phenyl]ethylamino]propanamide;
2-[2-[4-(2-fluorobenzyloxy)phenyl]ethylamino]propanamide;
2-[2-[3-(3-fluorobenzyloxy)phenyl]ethylamino]propanamide;
2-[2-[4-(3-fluorobenzyloxy)phenyl]ethylamino]propanamide;
single optical isomers thereof; and mixtures of single optical isomers thereof.

56. The method of claim 51, wherein the compound or its pharmaceutically acceptable salt is selected from:
2-[3-(2-fluorobenzyloxy)benzylamino]acetamide;
2-[4-(2-fluorobenzyloxy)benzylamino]acetamide;
2-[3-(3-fluorobenzyloxy)benzylamino]acetamide;
2-[4-(3-fluorobenzyloxy)benzylamino]acetamide;
2-[3-(2-fluorobenzyloxy)benzylamino]propanamide;
2-[4-(2-fluorobenzyloxy)benzylamino]propanamide;
2-[3-(3-fluorobenzyloxy)benzylamino]propanamide;
2-[4-(3-fluorobenzyloxy)benzylamino]propanamide;

(S)-(+)-2-[3-(2-fluorobenzyloxy)benzylamino]propanamide;
(S)-(+)-2-[4-(2-fluorobenzyloxy)benzylamino]propanamide;
(R)-(−)-2-[3-(2-fluorobenzyloxy)benzylamino]propanamide;
(R)-(−)-2-[4-(2-fluorobenzyloxy)benzylamino]propanamide;
(S)-(+)-2-[3-(3-fluorobenzyloxy)benzylamino]propanamide;
(S)-(+)-2-[4-(3-fluorobenzyloxy)benzylamino]propanamide;
(R)-(−)-2-[3-(3-fluorobenzyloxy)benzylamino]propanamide;
(R)-(−)-2-[4-(3-fluorobenzyloxy)benzylamino]propanamide;
2-[3-(2-fluorobenzyloxy)-4-methyl-benzylamino]propanamide;
2-[4-(2-fluorobenzyloxy)-3-methyl-benzylamino]propanamide;
2-[3-(3-fluorobenzyloxy)-4-methyl-benzylamino]propanamide;
2-[4-(3-fluorobenzyloxy)-3-methyl-benzylamino]propanamide;
2-[3-(2-fluorobenzyloxy)benzylamino]-N,N-dimethyl-propanamide;
2-[4-(2-fluorobenzyloxy)benzylamino]-N,N-dimethyl-propanamide;
2-[3-(3-fluorobenzyloxy)benzylamino]-N,N-dimethyl-propanamide;
2-[4-(3-fluorobenzyloxy)benzylamino]-N,N-dimethyl-propanamide;
2-[3-(2-fluorobenzyloxy)benzylamino]isovaleramide;
2-[4-(2-fluorobenzyloxy)benzylamino]isovaleramide;
2-[3-(3-fluorobenzyloxy)benzylamino]isovaleramide;
2-[4-(3-fluorobenzyloxy)benzylamino]isovaleramide;
2-[3-(2-fluorobenzyloxy)benzylamino]-3-hydroxy-propanamide;
2-[4-(2-fluorobenzyloxy)benzylamino]-3-hydroxy-propanamide;
2-[3-(3-fluorobenzyloxy)benzylamino]-3-hydroxy-propanamide;
2-[4-(3-fluorobenzyloxy)benzylamino]-3-hydroxy-propanamide;
2-[2-(4-pentylphenyl)ethylamino]propanamide;
2-[2-[3-(2-fluorobenzyloxy)phenyl]ethylamino]acetamide;
2-[2-[4-(2-fluorobenzyloxy)phenyl]ethylamino]acetamide;
2-[2-[3-(3-fluorobenzyloxy)phenyl]ethylamino]acetamide;
2-[2-[4-(3-fluorobenzyloxy)phenyl]ethylamino]acetamide;
single optical isomers thereof; and mixtures of single optical isomers thereof.

57. The method of claim 51, wherein the compound or its pharmaceutically acceptable salt is selected from:
2-[4-(2-fluorobenzyloxy)benzylamino]acetamide;
2-[4-(3-fluorobenzyloxy)benzylamino]acetamide;
2-[4-(2-fluorobenzyloxy)benzylamino]propanamide;
2-[4-(3-fluorobenzyloxy)benzylamino]propanamide;
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide;
2-[4-(2-fluorobenzyloxy)-3-methyl-benzylamino]propanamide;
2-[4-(3-fluorobenzyloxy)-3-methyl-benzylamino]propanamide;
2-[4-(2-fluorobenzyloxy)benzylamino]-N,N-dimethyl-propanamide;
2-[4-(3-fluorobenzyloxy)benzylamino]-N,N-dimethyl-propanamide;
2-[2-(4-pentylphenyl)ethylamino]propanamide;
single optical isomers thereof; and mixtures of single optical isomers thereof.

58. The method of claim 51, wherein the compound or its pharmaceutically acceptable salt is selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide; and
(R)-(−)-2-[4-(3-fluorobenzyloxy)benzylamino]propanamide.

59. The method of claim 51, wherein the compound is selected from:
(S)-(+)-2-[4-(2-fluorobenzyloxy)benzylamino]propanamide
or the pharmaceutically acceptable salt thereof with methanesulfonic acid.

60. The method of claim 51, wherein the compound is a pharmaceutically acceptable salt with methanesulfonic acid.

61. The method of claim 51, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

62. The method of claim 51, further comprising administering of second therapeutic agent which is an anxiolytic agent.

63. The method of claim 62, wherein the compound is (S)-(+)-2-[4-(2-fluorobenzyloxy)benzylamino]propanamide or the pharmaceutically acceptable salt thereof with methanesulfonic acid and the anxiolytic agent is a benzodiazepine, buspirone, or a beta-adrenergic receptor agonist.

64. The method of claim 61, wherein the compound is (S)-(+)-2-[4-(2-fluorobenzyloxy)benzylamino]propanamide or the pharmaceutically acceptable salt thereof and the second therapeutic agent is haloperidol or risperidone.

65. The method of claim 64, wherein the pharmaceutically acceptable salt is the salt with methanesulfonic acid, and the second therapeutic agent is haloperidol.

66. The method of claim 51, further comprising administering of a second therapeutic agent which is lithium, lamotrigine or valproate.

67. A method of treating schizophrenia combined with anxiety, comprising administering to a patient in need thereof of a therapeutically effective dose of a compound selected from:
(S)-(+)-2-[4-(2-fluorobenzyloxy)benzylamino]propanamide;
(S)-(+)-2-[4-(3-fluorobenzyloxy)benzylamino]propanamide;
(R)-(−)-2-[4-(2-fluorobenzyloxy)benzylamino]propanamide;
(R)-(−)-2-[4-(3-fluorobenzyloxy)benzylamino]propanamide; or a pharmaceutically acceptable salt thereof.

68. The method of claim 67, wherein the compound is a pharmaceutically acceptable salt with methanesulfonic acid.

69. The method of claim 67, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

70. The method of claim 67, further comprising administering of a second therapeutic agent which is an anxiolytic agent.

71. The method of claim 70, wherein the compound is (S)-(+)-2-[4-(2-fluorobenzyloxy)benzylamino]propanamide or the pharmaceutically acceptable salt thereof with methanesulfonic acid and the anxiolytic agent is a benzodiazepine, buspirone, or a beta-adrenergic receptor agonist.

72. The method of claim 69, where the second therapeutic agent is haloperidol or risperidone.

73. The method of claim 72, where the second therapeutic agent is haloperidol.

74. The method of claim 69, where the second therapeutic agent is lithium, lamotrigine or valproate.

75. A method of treating schizophrenia combined with anxiety, comprising administering to a patient in need thereof of a therapeutically effective dose of
(S)-(+)-2-[4-(2-fluorobenzyloxy)benzylamino]propanamide or
the pharmaceutically acceptable salt thereof with methanesulfonic acid.

76. The method of claim 75, further comprising administering of a second therapeutic agent which is a typical or atypical antipsychotic, a mood stabilizer, a serotonin receptor modulator, an AMPA modulator, a nicotinic receptor agonist, or a cholinesterase inhibitor.

77. The method of claim 75, further comprising administering of a second therapeutic agent which is an anxiolytic agent.

78. The method of claim 77, wherein the anxiolytic agent is a benzodiazepine, buspirone, or a beta-adrenergic receptor agonist.

79. The method of claim 76, wherein the second therapeutic agent is haloperidol or risperidone.

80. The method of claim 79, wherein the second therapeutic agent is haloperidol.

81. The method of claim 76, wherein the second therapeutic agent is lithium, lamotrigine or valproate.

* * * * *